United States Patent
Hamill

(10) Patent No.: US 7,378,661 B2
(45) Date of Patent: May 27, 2008

(54) ASYMMETRICAL POSITRON EMISSION TOMOGRAPH DETECTORS

(75) Inventor: James J. Hamill, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/247,626

(22) Filed: Oct. 11, 2005

(65) Prior Publication Data

US 2007/0080295 A1   Apr. 12, 2007

(51) Int. Cl.
  *G01T 1/164* (2006.01)
(52) U.S. Cl. ................................. 250/363.03
(58) Field of Classification Search ............ 250/363.03
  See application file for complete search history.

(56) References Cited

U.S. PATENT DOCUMENTS

| | | |
|---|---|---|
| 4,707,786 A | 11/1987 | Dehner |
| 4,833,327 A | 5/1989 | Hart |
| 5,291,021 A | 3/1994 | Tanaka et al. |
| 5,591,977 A | 1/1997 | Green et al. |
| 5,822,393 A | 10/1998 | Popescu |
| 5,867,555 A | 2/1999 | Popescu et al. |
| 6,362,479 B1 | 3/2002 | Andreaco et al. |
| 6,552,349 B2 | 4/2003 | Gagnon et al. |
| 6,700,468 B2 | 3/2004 | Crozier et al. |
| 6,710,349 B2 | 3/2004 | Shao |
| 2004/0097800 A1 * | 5/2004 | Crosetto ..................... 600/407 |

OTHER PUBLICATIONS

J.G. Colsher, "Fully Three-Dimensional Positron Emission Tomography" Phys. Med Biol, (1980) vol. 25, No. 1, pp. 103-115.
Joel S. Karp, et al., "Continuous Slice PENN-PET: A Positron Tomograph with Volume Imaging Capability" J Nucl Med (May 1990) vol. 31 No. 5 p. 617-627, Uni. of Pennsylvania, Philadelphia, PA.
D.W. Townsend, et al., "Three-Dimensional Reconstruction of PET Data from a Multi-ring Camera" Transactions on Nuclear Science (Feb. 1989) vol. 36, No. 1 pp. 1056-1065.
D.W. Townsend,et al., "Aspects of Three Dimensional Reconstruction for a Multi-Ring Positron Tomograph" Eur J Nucl Med (1989) vol. 15 pp. 741-745.

* cited by examiner

*Primary Examiner*—Constantine Hannaher

(57) ABSTRACT

An apparatus for detecting a greater number of lines of response (LOR) within a subset of azimuthal angles of a positron emission tomography scanner. In a positron emission tomography (PET) scanner, the detectors are configured to detect a greater number of lateral LORs than the number of anterior/posterior LORs passing through a patient. The increased sensitivity to the lateral LORs compensates for the increased distance that the lateral LORs travel through the patient than the anterior/posterior LORs. In one embodiment, at least one pair of partial rings are positioned adjacent fixed detector rings. In another embodiment, panel detectors with a longer length than the other detectors are positioned to be responsive to the lateral LORs. In still another embodiment, detectors rotated with a variable angular speed, spending more time measuring lateral LORs than measuring anterior/posterior LORs.

19 Claims, 6 Drawing Sheets

ASYMMETRICAL POSITRON EMISSION TOMOGRAPH DETECTORS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention pertains to a positron emission tomography (PET) detector assembly configuration, or tomograph, for increasing the sensitivity within a subset of azimuthal angles. More particularly, this invention pertains to a PET scanner with a set of detectors configured to detect a greater number of lines of response (LORs) within a first set of azimuth angles than the number of LORs within a second set of azimuth angles. The LORs within the first set of azimuth angles are subject to a greater amount of attenuation than the other LORs because the LORs within the first set of azimuth angles travel a longer distance through the patient and the increased sensitivity compensates for this attenuation.

2. Description of the Related Art

Positron Emission Tomography (PET) is a nuclear imaging technique used in the medical field to assist in the diagnosis of diseases. PET allows the physician to examine the whole patient at once by producing pictures of many functions of the human body unobtainable by other imaging techniques. In this regard, PET displays images of how the body works (physiology or function) instead of simply how it looks. PET is considered the most sensitive, and exhibits the greatest quantification accuracy, of any nuclear medicine imaging instrument available at the present time. Applications requiring this sensitivity and accuracy include those in the fields of oncology, cardiology, and neurology.

In PET, short-lived positron-emitting isotopes, referred to as radiopharmaceuticals, are injected into a patient. When these radioactive drugs are administered to a patient, they distribute within the body according to the physiologic pathways associated with their stable counterparts. As the radiopharmaceutical isotopes decay in the body, they discharge positively charged particles called positrons. Upon discharge, the positrons encounter electrons, and both are annihilated. As a result of each annihilation event, gamma rays are generated in the form of a pair of diametrically opposed photons approximately 180 degrees (angular) apart. After the PET scanner detects these annihilation "event pairs" over a period of time, the isotope distribution in a cross section of the body is reconstructed. These events are mapped within the patient's body, thus allowing for the quantitative measurement of metabolic, biochemical, and functional activity in living tissue. More specifically, PET images (often in conjunction with an assumed physiologic model) are used to evaluate a variety of physiologic parameters such as glucose metabolic rate, cerebral blood flow, tissue viability, oxygen metabolism, and in-vivo brain neuron activity.

Mechanically, a PET scanner consists of a bed, or gurney, and a gantry supporting the tomograph detectors. In some tomographs, the gantry is inside an enclosure having a tunnel through its center, through which the bed traverses. In other tomographs, the detectors are cantilevered over the front of the gantry. In all types of tomographs, the gantry defines a tunnel through which the patient travels. The patient, who has been treated with a radiopharmaceutical, lies on the bed and is moved longitudinally past the detectors. Modern PET tomographs measure the radiation emerging from the patient along a large number of lines of response (LOR), each of which is characterized by four numbers: a radial coordinate, specifying how far the line is from the tomograph's main axis; an azimuthal angle defining the tilt of the LOR in a plane transverse to that axis; an axial coordinate defining the axial position of the LOR's midpoint; and a co-polar angle defining the LOR's tilt angle with respect to the transverse plane. Tomographs can operate either two dimensionally (2D) or three dimensionally (3D). In the 2D case, septa are used to block radiation at large co-polar angles. In the 3D case, no such septa are used. The scanner's sensitivity, and hence its ability to make a good image, is mainly determined by the amount of time that a given body portion of the patient sits before the scanner, and in the 3D case, by the range of co-polar angles, with a larger range corresponding to greater sensitivity. A tomograph's sensitivity is increased by making it relatively longer in the axial direction, so that each body portion of the patient can be scanned for a larger fraction of the total study time. In the case of 3D imaging, the sensitivity is further increased by increasing the scanner length, since this allows the measurement of a greater range of co-polar angles. The combination of the two effects means that the scanner's sensitivity in whole-body imaging scales with the square of its length.

There are four classes of PET tomographs, based on the arrangement of the detectors. Fixed-ring scanners have numerous small detectors organized in detector blocks, which are grouped into buckets, and arranged in an arc around the circumference of the gantry. A second class of PET tomographs includes fixed polygonal arrangements of panel detectors. A third class includes detectors arranged in an arc around the circumference of the gantry, with the detectors rotating about the axis of the gantry. A fourth class includes polygonal arrangements of panel detectors, with the panel detectors rotating about the axis of the gantry.

In each case, the tomograph samples all directions with nearly the same sensitivity. Although it is a simple symmetry for the scanner, this perfect balance is not optimal for whole-body imaging because cross-sections of the body are not symmetrical. That is, the patient's body typically has a greater lateral dimension than an anterior/posterior dimension, when it is imaged with the patient in a horizontal position in the scanner. Accordingly, radiation directed in horizontal and nearly horizontal (lateral) lines of response (LOR's) is strongly attenuated by the patient's body, whereas the radiation in vertical and nearly vertical (anterior/posterior) LOR's is less strongly attenuated. The asymmetry in the measured radiation, combined with the symmetry of the instrument, leads to an undesirable situation in which the data are measured with unequal statistical accuracy. One consequence of this situation is well known to people who read PET images: horizontal streaks across the image in reconstructions done by the filtered backprojection method. These streaks are a common artifact in whole-body PET imaging.

Various articles have been written documenting the processing of data from both ring detector and panel detector scanners. The following articles are representative of the types of scanners and methods of using and processing the LOR data obtained from the detectors. An early reference to the problem of reconstructing images from multi-ring PET scanners is J. G. Colsher, "Fully three-dimensional positron emission tomography," Phys Med Biol., vol. 25, no. 1, (1980) pp. 103-15. The Colsher paper presents a mathematical algorithm for performing fully three-dimensional positron emission tomography with ring-type scanners. An early description of fully three dimensional (non iterative) reconstruction is by D. Townsend, et al., "Aspects of three dimensional reconstruction for a multi ring positron tomograph," Eur. J. Nucl. Med., vol. 15, (1989), pp. 741-45. Also, another description is by D. Townsend, et al., "Three Dimensional Reconstruction of PET Data from a Multi-Ring Camera," IEEE Transactions on Nucl. Sci., vol. 36, no. 1, (February 1989), pp. 1056-65. An early description of polygonally arranged detectors is of the so-called PENN-PET design at the University of Pennsylvania by J. S. Karp, et al., "Continuous-Slice PENN-PET: a Positron Tomograph with Volume Imaging Capability," J. Nucl. Med., vol. 31, no. 5, (May 1990), pp. 617-27. The Karp paper discusses a scanner with six hexagonally arranged detector panels.

BRIEF SUMMARY OF THE INVENTION

A detector assembly configuration for increasing the sensitivity within a subset of azimuthal angles of a positron emission tomography (PET) scanner is provided. In one embodiment, an asymmetrical configuration of detector rings includes a partial ring adjacent to a full detector ring. The partial ring is responsive to lateral lines of response (LORs) that are subject to a greater amount of attenuation because the lateral LORs travel a greater distance through the patient than the anterior/posterior LORs. In one such embodiment, a pair of partial rings are located diametrically opposite each other. In another embodiment, pairs of partial rings are located on opposite sides of the full rings. That is, viewing the full rings along the central axis, the pairs of partial rings are located on the front and the back sides of the full rings.

In another embodiment, panel detectors are used in which the panel detectors responsive to the lateral LORs have a longer axial length than the panel detectors response to the anterior/posterior LORs.

In still another embodiment, the detectors rotate about a space for receiving a patient. The detectors rotate around a central axis with at least two different speeds. The detectors have a first angular speed when the detectors are positioned to be responsive to the lateral LORs and a second angular speed when the detectors are positioned to be responsive to the anterior/posterior LORs. The first angular speed is slower than the second angular speed, thereby allowing the detectors to measure a greater number of lateral LORs than anterior/posterior LORs because the detectors are favorably positioned to detect the lateral LORs for a longer time than the detectors are positioned to detect the anterior/posterior LORs. In various embodiments, the rotating detectors are panel detectors, partial detector rings, or other shapes suitable for PET scanning.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

An apparatus for increasing the sensitivity within a subset of azimuthal angles of a positron emission tomography (PET) scanner 10 is disclosed. The subset of azimuthal angles includes a set of azimuth angles through which travel the lines of response that are subject to the most attenuation, for example, those lines of response that travel the greatest distance through a patient. The concept described herein is readily adapted to the various types of PET scanners. Various embodiments of scanners 10 are illustrated in the figures. The invention is suitable for use to obtain two-dimensional images, such as with septa retracted, and to obtain three-dimensional images, such as with septa extended.

Figure 1:
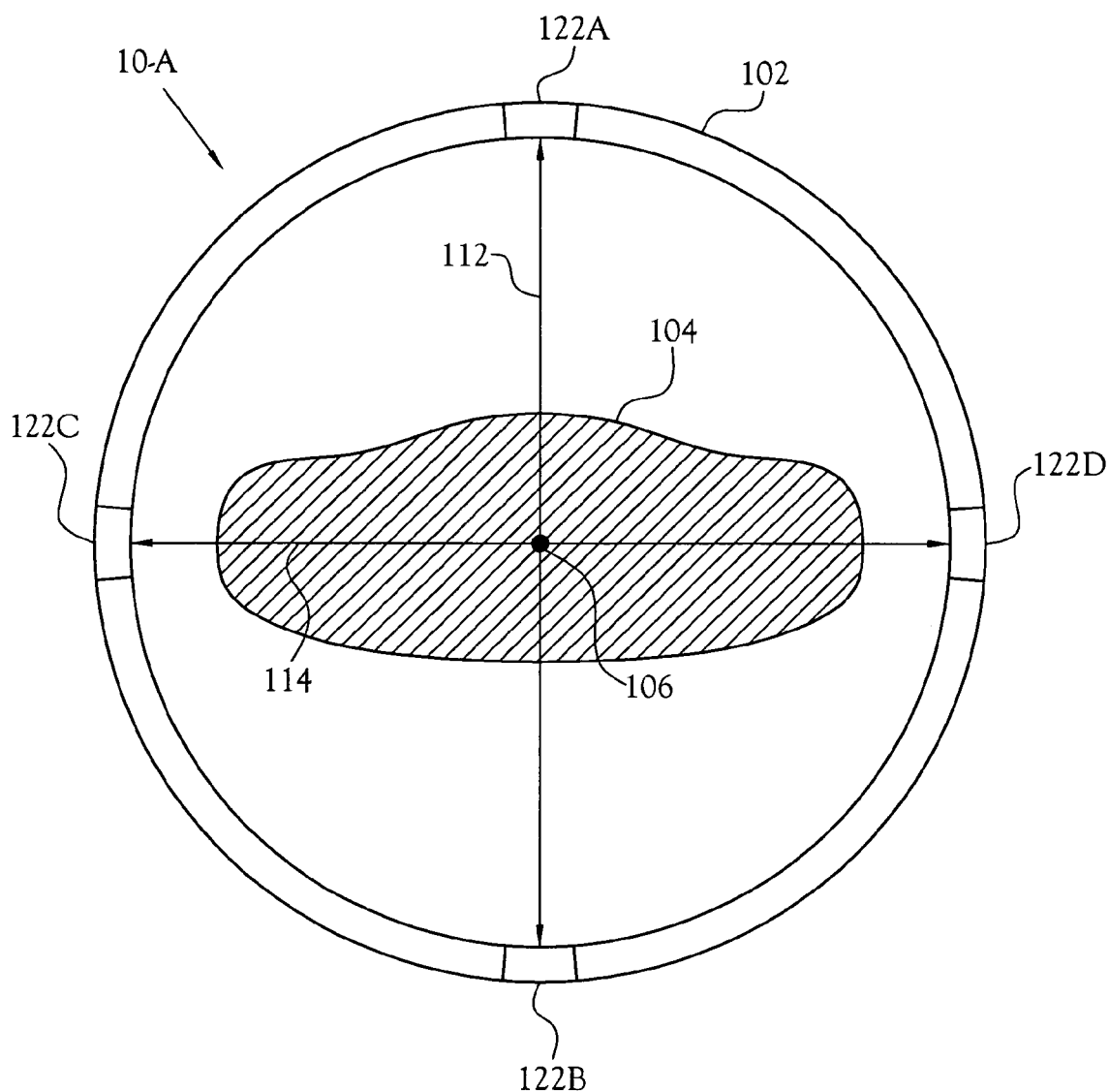
FIG. 1 is an axial cross-sectional view of a body within a detector ring.
Figure 7:
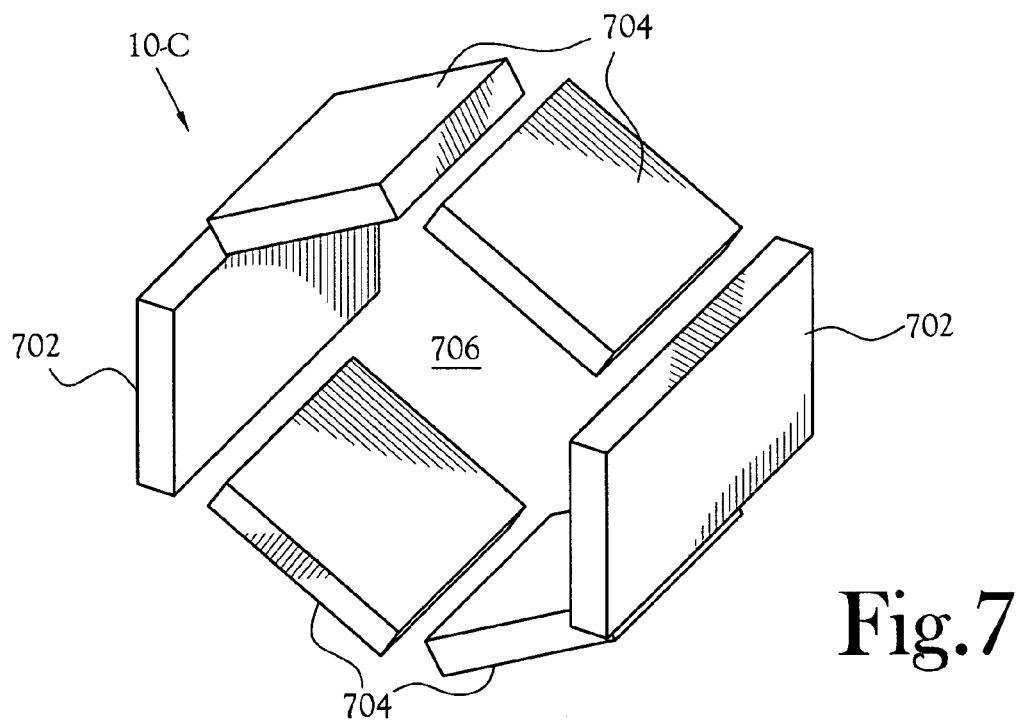
FIG. 7 is a perspective view of an embodiment of a scanner with panel detectors.

FIG. 1 illustrates an axial cross-sectional view of a body 104 within a detector ring 102. The PET scanner 10-A is the type with detectors 122 arranged around a patient 104 in a ring configuration. In another embodiment, the detectors 122 are arranged around the patient in a polygonal configuration, such as illustrated in FIG. 7. In the illustrated embodiment, the detectors 122 do not rotate about the patient 104, but maintain a fixed radial position relative to the patient 104. A patient 104 is within the volume, or space, defined by the detector rings 102 of a PET scanner 10-A. The detector rings 102 contain a plurality of sensors, or detectors, 122A, 122B, 122C, 122D of which only four are illustrated in FIG. 1. The detectors 122 are responsive to the photons emitted by an annihilation event caused by a radiopharmaceutical inside the patient 104. The detectors 122 are in communication with the processing system of the PET scanner 10.

The typical patient 104 is positioned flat on his back, which results in the patient 104 having a wider cross-section than the cross-section is tall, that is, the lateral dimension is greater than the anterior/posterior dimension. The line defining the lateral dimension is oriented 90° from the line defining the anterior/posterior dimension. Although the terms lateral and anterior/posterior are used throughout the discussion of the various embodiments, it is recognized that there are cases in which the lateral dimension is less than the anterior/posterior dimension, such as when scanning the skull. Accordingly, the lateral dimension is to be interpreted to be the dimension of the measured object or body part that is greater than the dimension that is along a line oriented 90° from the line of the lateral dimension, with both the lateral dimension and the anterior/posterior dimension in a plane parallel to the detector rings 102. Likewise, the anterior/ posterior dimension is to be interpreted to be the dimension of the measured object or body part that is less than the lateral dimension.

The illustrated lines of response (LOR) 112, 114 pass through the center 106 of the patient 104 and are orthogonal to a line from the patient's feet to head. Generally, the cross-section of the patient 104 roughly assumes an ellipse with the major axis being the lateral dimension and the minor axis being the anterior/posterior dimension. One lateral LOR 114 passes through the major axis and the other, anterior/posterior LOR 112 passes through the minor axis. The lateral LOR 114 falls within a first set of azimuth angles that includes the LORs 114 that potentially pass through the thickest portion of the patient 104. The anterior/posterior LOR 112 falls within a second set of azimuth angles that includes the LORs 112 that potentially pass through the thinnest portion of the patient 104. In one embodiment, the first set of azimuth angles corresponds to the angle of those LORs 114 with an azimuth angle equal to or less than 45 degrees relative to the illustrated horizontal axis. The second set of azimuth angles corresponds to the angle of those LORs 112 with an azimuth angle greater than 45 degrees relative to the illustrated horizontal axis. In other embodiments, the angles of the LORs 114, 112 passing through the first set of azimuth angles and the second set of azimuth, respectively, are defined by the cross-sectional areas of interest for a patient.

The LORs 112, 114 are detected by pairs of sensors 122 in the detector rings 102. During a scan, a positron emitted by a radiopharmaceutical encounters an electron and the resulting annihilation event releases two photons moving approximately in opposite directions. The path of these two photons is an LOR 112, 114. Unless they interact with the patient's body in a process called scattering or attenuation, the photons following the LOR 112, 114 strike a pair of sensors, or detectors, 122A and 122B, 122C and 122D in the detector rings 102.

Using the orientation illustrated in FIG. 1, the horizontal, or lateral, LOR 114 extends a greater distance through the patient 104 than the vertical, or anterior/posterior, LOR 112. Accordingly, the lateral LOR 114 is attenuated more than the anterior/posterior LOR 112. However, the illustrated symmetrical, circular detector rings 102 measures the radiation of the various LORs 112, 114 without regard to any attenuation caused by asymmetrical bodies of the patient 104.

Figure 2:
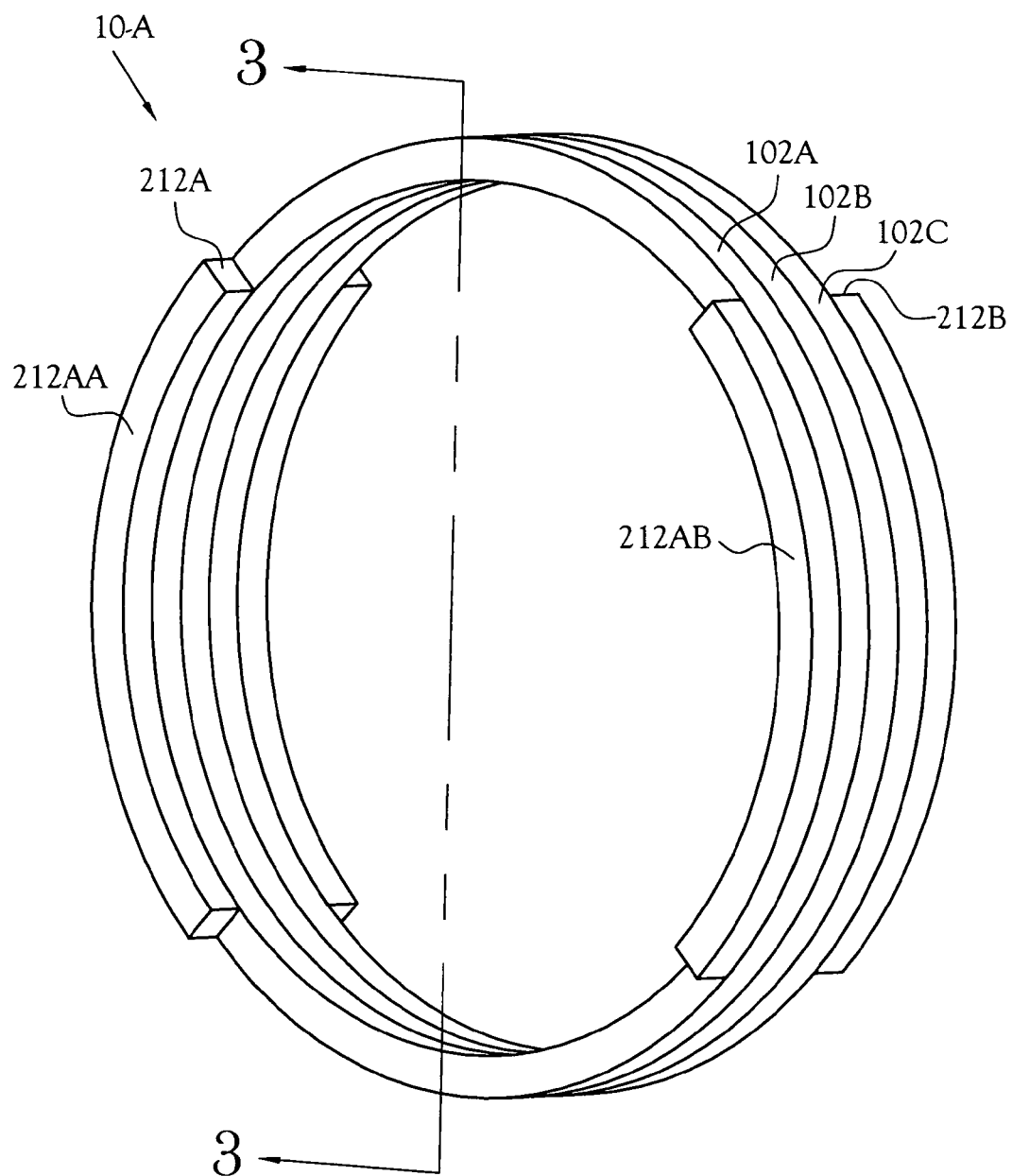
FIG. 2 is a perspective view of one embodiment of the detector rings.
Figure 3:
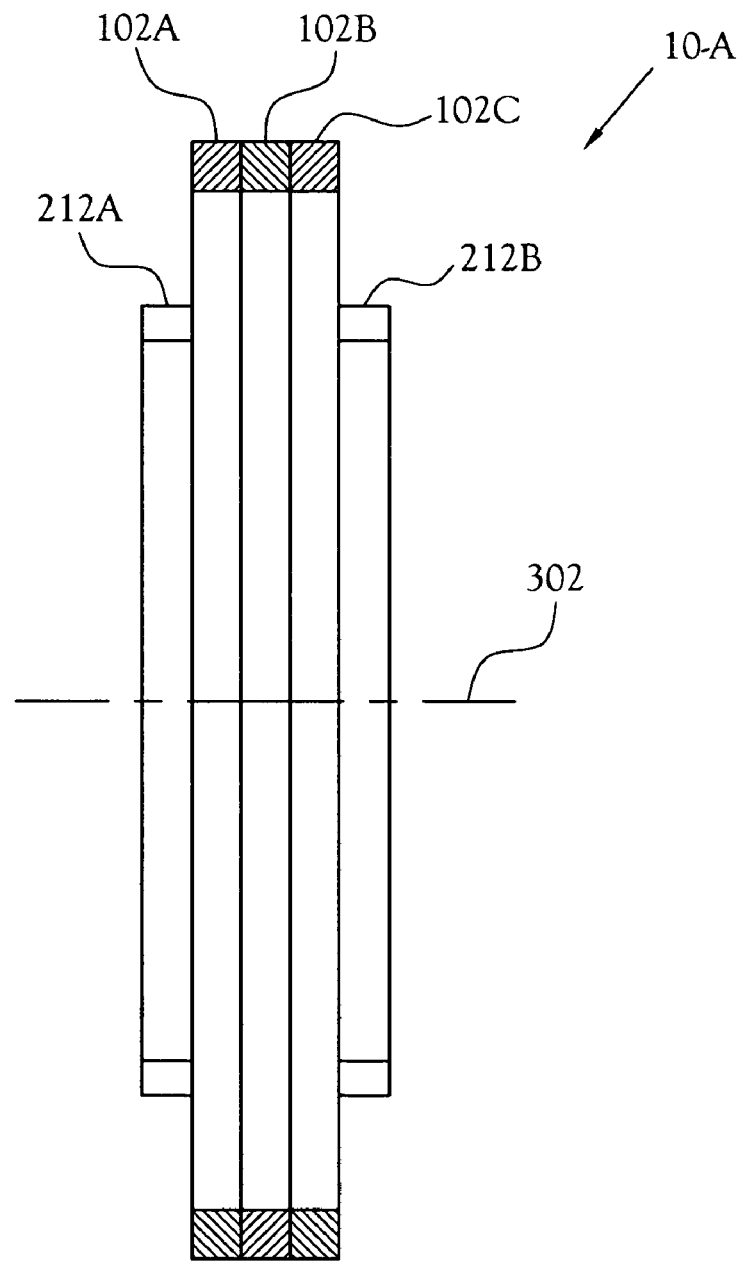
FIG. 3 is a cross-sectional view of the detector rings of FIG. 2.

FIG. 2 illustrates a perspective view of one embodiment of the detector assembly 10-A showing its asymmetry with two pairs of partial rings 212. FIG. 3 illustrates a cross-sectional view of the detector assembly 10-A of FIG. 2. It is noted that FIG. 1 illustrates an axial view of a single, full ring 102 and does not show the pair of partial rings 212. In the illustrated embodiment, the PET scanner has a set of adjacent circular detector rings 102A, 102B, 102C. Those skilled in the art will recognize that the number of rings 102 varies in PET scanners and that the number of rings 102 illustrated is three only in order to simplify discussing the invention. Further, those skilled in the art will recognize that the rings 102 need not be circular, but may have an elliptical or other shape, as seen from an axial view, although the rings 102 are illustrated as circular in the figures. The detector rings 102 enclose a space, or volume, with a longitudinal axis 302. In the illustrated embodiment, the longitudinal axis 302 intersects the center 106 of the patient 104.

Adjacent to the outer detector rings 102A, 102C are partial detector rings 212A, 212B. The partial detector rings 212 do not encircle the patient 104, but are positioned to be receptive to LORs 114 traversing the widest portion of the patient 104. In various embodiments, the number of pairs of partial detector rings 212 will vary from a single pair of partial detector rings 212A, 212B on each side of the full rings 102, to a single pair of partial detector rings 212A on one side of the full rings 102, to multiple pairs of partial detector rings 212A, 212B on one or both sides of the full rings 102.

Each pair of partial rings 212A, 212B in the illustrated embodiment forms two arc segments 212AA, 212AB, with each arc segment 212AA, 212AB positioned substantially diametrically opposite the other arc segment 212AB, 212AA. The pairs of partial rings 212 are positioned such that the detectors 122C, 122D are responsive to the photons traveling along the LORs 114 that traverse the major axis of a slice through the patient 104. Each arc segment 212AA, 212AB contains substantially the same number of detectors 122C, 122D as the other. The asymmetrical configuration of the full rings 102 and the partial rings 212 allows for more sensitivity of the scanner 10-A in the lateral direction than the anterior/posterior direction, which compensates for the greater distance the lateral LORs 114 travel through the patient 104.

Figure 4:
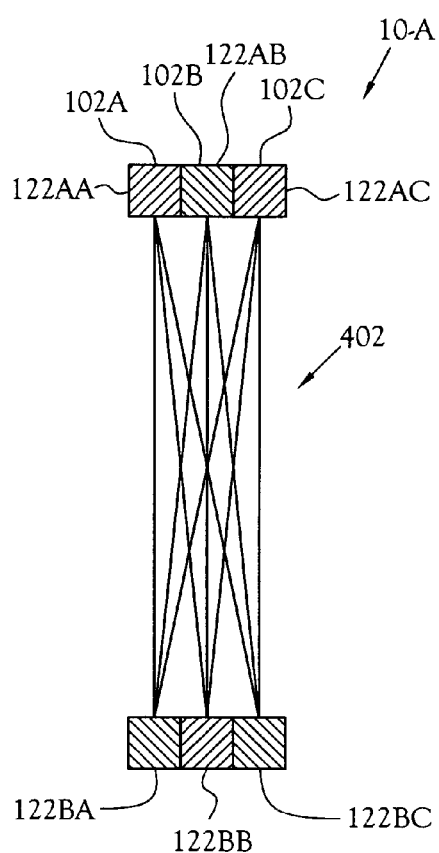
FIG. 4 is a pictorial view of the lines of response for three rings.
Figure 8:
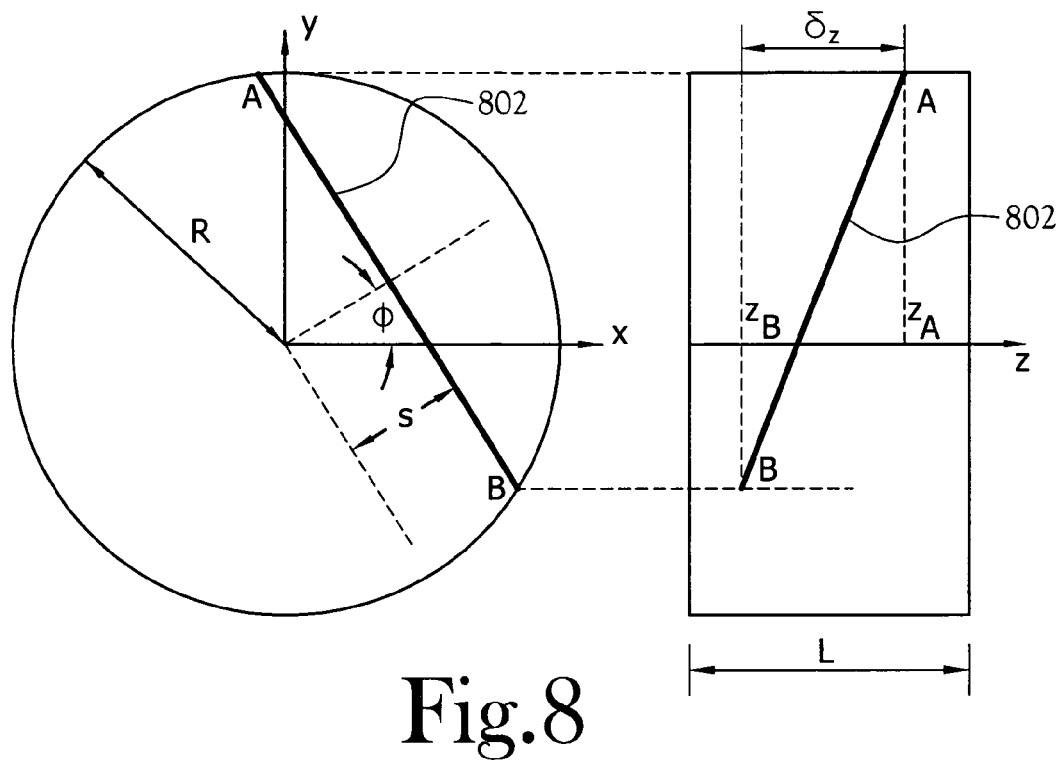
FIG. 8 shows the geometry of a cylindrical PET scanner.
Figure 9:
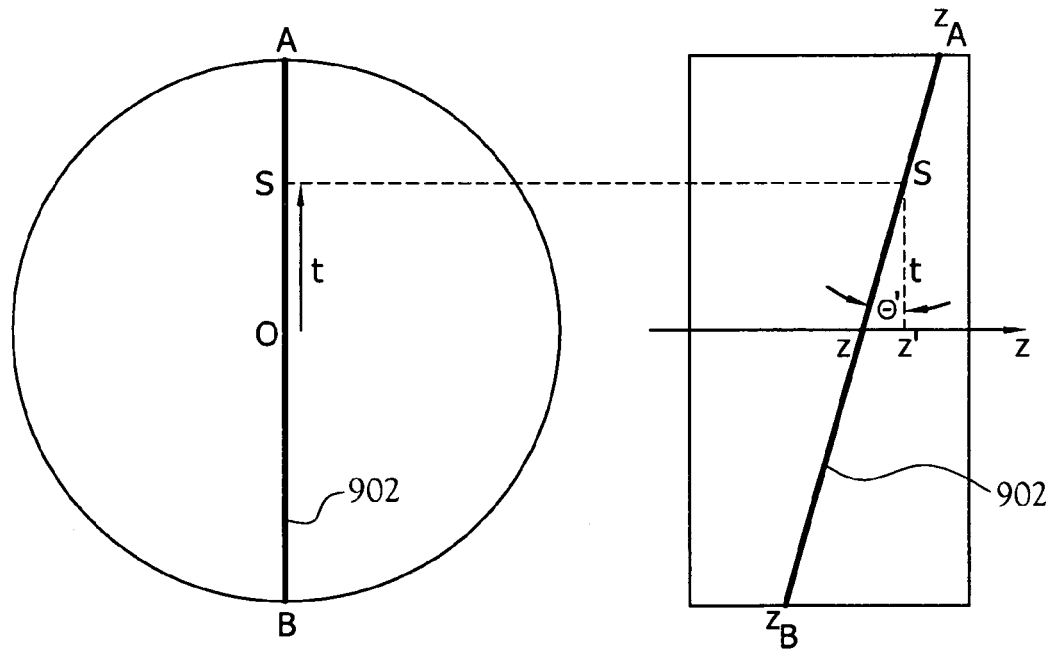
FIG. 9 shows the geometrical interpretation of three-dimensional PET acquisition geometry.

FIG. 4 illustrates a pictorial view of the lines of response 402 for three rings 102. To simplify the description of this embodiment, only a single detector 122 in a detector block is discussed. A detector block spans the width of each ring 102 and contains many detectors 122. Because each block contains many individual crystal elements, thousands of LORs may be defined between the numerous detectors 122 of any two blocks. For illustration purposes and to simplify the discussion, a single detector 122 in each block is used to illustrate the various LORs 402, 502 between the opposing blocks. Those skilled in the art will recognize that possible lines of response are not limited to only opposing blocks; however, this discussion, for simplicity, only discusses LORs 402, 502 between opposing blocks. FIGS. 8 and 9 illustrate the geometry of cylindrical PET scanners and the variables associated with a line of response.

A side cross-sectional view of the detector rings 102 is shown in FIG. 4, along with each of the possible lines of response 402 between a single detector 122 in a detector block on each side of each ring 102A, 102B, 102C. Each detector 122 in one plane of the grouping of three detector rings 102 is responsive to three LORs 402. The detector 122AA at the top of the first detector ring 102A is responsive to a photon traveling along a line of response between that detector 122AA and a detector 122BA at the bottom of that detector ring 102A. The detector 122AA is also responsive to a photon traveling along a line of response between that detector 122AA and a detector 122BB at the bottom of the adjacent, second detector ring 102B. Likewise, the detector 122AA is also responsive to a photon traveling along a line of response between that detector 122AA and a detector 122BC at the bottom of the next adjacent, third detector ring 102C. There are a total of nine LORs 402 associated with the six detectors 122AA, 122AB, 122AC, 122BA, 122BB, 122BC.

Figure 5:
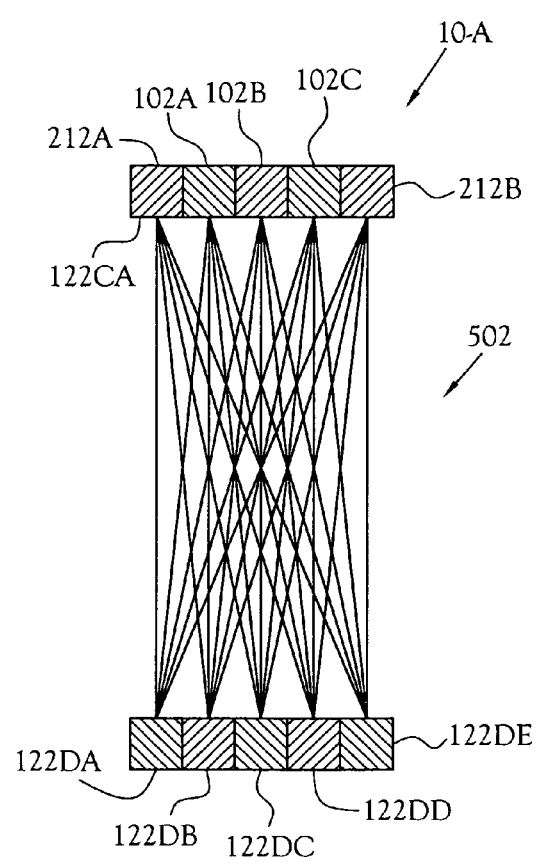
FIG. 5 is a pictorial view of the lines of response for five rings.

FIG. 5 illustrates a pictorial view of the lines of response 502 for five detector rings 102, 212. A top cross-sectional view of the detector assembly 10 is shown in FIG. 5, along with each of the possible lines of response 502 between a single detector 122 on each side of each ring 102A, 102B, 102C, 212A, 212B. Each detector 122 in one plane of the grouping of three full detector rings 102 and two partial detector rings 212 is responsive to five LORs 502. For example, the detector 122CA is responsive to LORs 502 between that detector 122CA and the opposite detectors 122DA, 122DB, 122DC, 122DD, 122DE. There are a total of twenty-five LORs 502 associated with the three detector rings 102A, 102B, 102C and two partial rings 212A, 212B, which is an increase of 2.8 times the number of the LORs 402 associated with three detector rings 102A, 102B, 102C.

Figure 6:
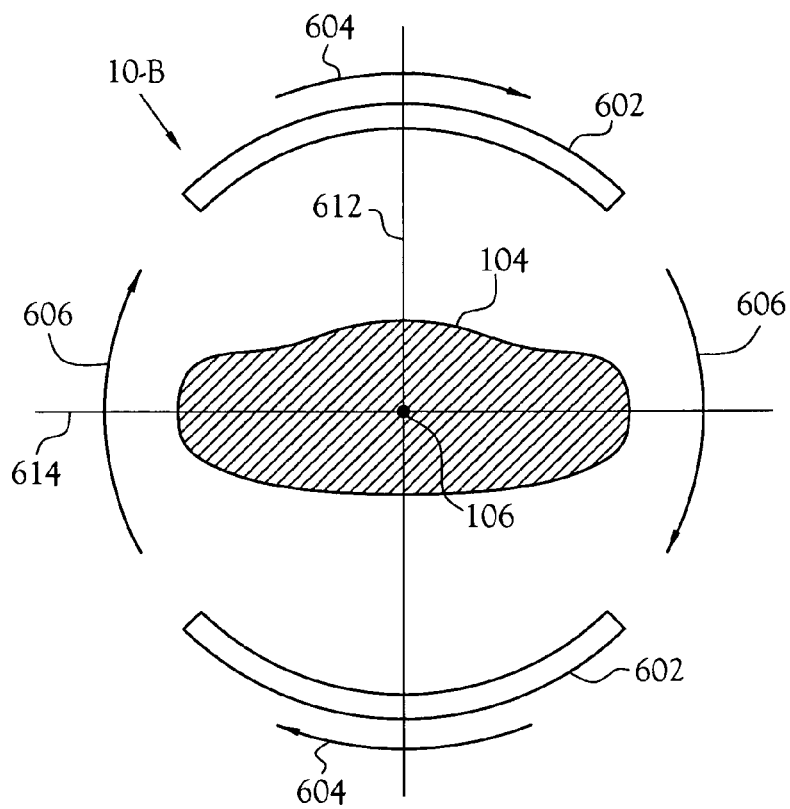
FIG. 6 is a pictorial side view of an embodiment of a scanner with rotating partial rings.

FIG. 6 is a pictorial side view of an embodiment of a scanner 10-B with partial rings 602. In the illustrated embodiment, a pair of generally opposed detector assemblies 602, illustrated as partial rings 602, rotate in a direction 606 around the central axis 106 of the scanner 10. In another embodiment, instead of partial rings 602 containing the detectors, or sensors, 122, flat panels or other arrays of detectors 122 rotate around the patient 104. In order to increase the sensitivity of the scanner 10-B to lateral LORs 114 relative to anterior/posterior LORs 112, the rotational speed of the partial rings 602 varies depending upon the position of the ring 602 relative to the patient 104. Because the amount of time a detector 122 spends within a specified area is directly related to the sensitivity of that detector 122, the rotational, or angular, speed 604, 606 of the partial rings 602 varies from a faster, or maximum, rotational speed 604 to a slower, or minimum, rotational speed 606 as the detectors 122 in the rings 602 move from areas that require less sensitivity to areas that require more sensitivity.

The rotational speed 604 of the partial rings 602 when measuring the anterior/posterior LORs 112 is faster than the rotational speed 606 of the partial rings 602 when they are measuring the lateral LORs 114. Referring to the position of the partial rings 602 as illustrated in FIG. 6, the rings 602 have a faster angular speed at the illustrated position than the rings 602 would have with the rings 602 rotated 90°. Accordingly, the dwell time of the partial rings 602 when detecting LORs 114 within the first set of azimuth angles is greater than the dwell time of the partial rings 602 when detecting LORs 112 within the second set of azimuth angles. The dwell time is the amount of time the rings 602 are at a specific position or within a range of positions. The LORs 114 within the first set of azimuth angles being those LORs 114 traveling the greatest distance through the patient 104, and the LORs 112 within the second set of azimuth angles being those LORs 112 traveling the shortest distance through the patient 104.

FIG. 7 is a perspective view of an embodiment of a scanner 10-C with panel detectors 702, 704. In this embodiment, the scanner 10-C uses panels of detectors 702, 704 to detect the LORs 112, 114 passing through the patient 104 who is in the volume, or space, 706 bounded by the panel detectors 702, 704. When viewed axially, the panels 702, 704 of the scanner 10-C form a polygonal shape.

The panel detectors 702, 704 have an asymmetrical configuration in which the, side, or lateral, panels 702 that are responsive to the lateral LORs 114 have a longer axial dimension than the panels 704 that are response to the anterior/posterior LORs 112. That is, the dimension of the lateral panels 702, as measured parallel to the center axis of the volume 706, is longer than the equivalent dimension of the other panels 704. Accordingly, in one embodiment the lateral panels 702 have a greater number of detectors 122 in a line parallel to the center axis than the other panels 704. This asymmetry allows the lateral panels 702 to measure more lateral LORs 114 than the other panels 704 measure anterior/posterior LORs 112.

In one embodiment, the panels 702, 704 include a rectangular array of 9 by 13 detector blocks, with each detector block having numerous detectors 122. In another embodiment, the scanner 10 includes eight lateral panels 702 (four on each side of the contained volume, or space, 706) and four other panels 704 (two on each side of the contained volume, or space, 706). Those skilled in the art will recognize that the number of lateral panels 702 and the number of panels 704 can vary without departing from the spirit and scope of the present invention. Further, those skilled in the art will recognize that the polygonal arrangement of the detector panels 702, 704 as seen axially is not required to be a regular polygon shape.

As illustrated in FIGS. 4 and 6, the increased sensitivity of the scanner 10 is due to the increased number of LORs 502 that are detected within a subset of azimuthal angles. The subset of azimuthal angles includes the set of azimuth angles through which the LORs 502 subject to the most attenuation travel, such as the lateral LORs 114 that travel through the thickest portion of a patient 104. The embodiments illustrated in FIGS. 1 to 5 and in FIG. 7 increase the sensitivity by increasing the number of detectors in a location where the detectors are responsive to the lateral LORs 114. The embodiment described with respect to FIG. 6 increases the sensitivity of the scanner 10 by increasing the time a rotating detector assembly 602 is favorably positioned to respond to lateral LORs 114 relative to the time the detector assembly 602 is positioned to respond to anterior/posterior LORs 112.

The asymmetry in the detector 122 configuration around the patient 104 enables the scanner to detect a greater number of LORs 114 falling within a first set of azimuth angles relative to the number of LORs 112 falling within a second set of azimuth angles. In the embodiment illustrated in FIG. 1, the lateral LOR 114 falls within the first set of azimuth angles and the anterior/posterior LOR 112 falls within the second set of azimuth angles. In one embodiment, the LOR 112, 114 data collected from the detectors 122 is used with fully three-dimensional iterative reconstruction in geometries with incomplete angular sampling. This reconstruction allows for the difference in the number of LORs 112, 114 detected to be used to reconstruct images while minimizing artifacts. The detected first set of LORs 114 and the detected second set of LORs 112 are combined by a processing system to produce an image.

In various embodiments the asymmetry is based on the number of detectors 122 physically located proximate the lateral dimension of the patient 104 and responsive to the LORs 114 within the first set of azimuth angles. In these embodiments, the number of detectors responsive to the LORs 114 within the first set of azimuth angles is greater than the number of detectors responsive to the LORs 112 within the second set of azimuth angles. These various embodiments include, but are not limited to, ring-based scanners 10-A as illustrated in FIGS. 1 to 5 and panel detector based scanners 10-C as illustrated in FIG. 7.

In other embodiments, the asymmetry is based on the time a selected number of detectors 122 are located proximate the lateral dimension of the patient 104 and responsive to the LORs 114 within the first set of azimuth angles. In these embodiments, the detectors 122 rotate or are moved around the patient 104 and the detectors 122 have a greater dwell time for detecting LORs 114 within the first set of azimuth angles than the detectors 122 have for detecting LORs 112 within the second set of azimuth angles. The dwell time being the time in which the detectors 122 are at one position or are in a position to be responsive to LORs 112, 114 within a selected set or range of azimuth angles. These various embodiments include, but are not limited to, rotating ring-based scanners 10-A as illustrated in FIG. 6 and panel detector based scanners 10-7 using the rotating panel concept as also illustrated in FIG. 6.

FIGS. 8 and 9 illustrate the geometry of cylindrical PET scanners and LORs 802, 902. FIG. 8 illustrates the geometry of a cylindrical PET scanner having a radius R and a length L. FIG. 8 includes a transaxial view (left side of figure) showing the x, y axes and the sinogram variables s and φ, and it includes a longitudinal view (right side of figure) showing the z axis and the sinogram variables z and Δ. In FIG. 8, a line of response (LOR) 802 is shown extending between two detectors A and B. The sinogram variable s, the radial coordinate, is the distance between the z axis and the projection of the LOR onto a transaxial plane, and φ is the angle between this projection and the y axis, which is equal to the angle of a line perpendicular to the projection of the LOR and the x axis. The azimuth angle with reference to the y axis is given by φ. The anterior/posterior LOR 112 illustrated in FIG. 1 has an azimuth angle of 0 degrees and the lateral LOR 114 illustrated in FIG. 1 has an azimuth angle of 90 degrees.

The longitudinal view of FIG. 8 shows the sinogram variable $\delta_z$ as the longitudinal distance between the two detectors A and B, or $z_A - z_B$, with $z_A$ being the location of one detector A along the z axis, measured from a point on the z axis, and $z_B$ being the location of the other detector B along the z axis, measured from the same point on the z axis. A fourth sinogram variable, z, not illustrated, is defined as $(z_A - z_B)/2$. Thus, z is the axial coordinate of the point mid-way between the two detectors, and $\delta_z$ is the axial spacing between the two detectors A and B. The set of data corresponding to a fixed pair (z, Δ) define an oblique sinogram, with the special case of $\delta_z = 0$ being called a direct sinogram. For a PET scanner with N rings, such as the 3 ring scanner illustrated in FIGS. 2, 3, and 4, each pair of rings corresponds to a fixed pair (z, $\delta_z$), and the data acquired in 3D mode consists of $N^2$ sinograms, which includes N direct sinograms and N·(N-1) oblique sinograms. The four sinogram parameters (s, φ, z, $\delta_z$) define a 3D sinogram. A 2D sinogram is restricted to LORs in the transaxial plane, so that $z_A = z_B$. Therefore, a 2D sinogram is defined by three parameters (s, φ, z). Reconstructing slices, or direct sinograms, from 2D data involves fewer parameters than reconstructing slices from 3D data.

FIG. 9 illustrates the geometry of a cylindrical PET scanner with a source S at a distance t from the axis z and a corresponding LOR 902. The axial position of the source S can be determined from the equation $z' = z + t \cdot \tan(\theta') = z + \delta \cdot t$, where z is the axial point midway between the detectors A and B and where δ is the tangent of the angle θ' between the LOR and the transaxial plane, called the ring difference.

The detector assembly 10 includes various functions. The function of detecting a greater number of LORs 114 within a first set of azimuth angles than LORs 112 within a second set of azimuth angles is implemented, in one embodiment, by a pair of partial detector rings 212A, 212B positioned adjacent the full detector rings 102, with the partial rings 212A, 212B positioned in-line with the lateral dimension of the patient 104. In another embodiment, the function is implemented by a group of detectors 122C, 122D positioned diametrically opposite each other such that LORs 114 passing within a first set of azimuth angles are sensed. The group of detectors 122C, 122D are positioned adjacent the detectors 122 surrounding the patient 104.

In still another embodiment, the function is implemented by panel detectors 702, 704 positioned around a space 706 for receiving a patient 104. The lateral panel detectors 702 have a longer axial length than the other panel detectors 704. The longer axial length allows the lateral panel detectors 702 to detect a greater number of LORs 114 within a first set of azimuth angles than the number of LORs 112 within a second set of azimuth angles detected by the other panel detectors 704.

In yet another embodiment, the function is implemented by detectors 602 rotating around a center point 106 with a variable angular speed. When the detectors 602 are rotating 604 in a position where the detectors 602 are responsive to LORs 112 within a second set of azimuth angles, the angular speed is greater than the angular speed when the detectors 602 are rotating 606 in a position where the detectors 602 are responsive to the LORs 114 within a first set of azimuth angles.

From the foregoing description, it will be recognized by those skilled in the art that an apparatus for increasing the sensitivity within a subset of azimuth angles of a positron emission tomography (PET) scanner has been provided. In various embodiments, the configuration of the detectors 122 are such that a greater number of LORs 114 within a first set of azimuth angles are measured than the number of LORs 112 in a second set of azimuth angles. This increased sensitivity to select LORs 114 compensates for the increased distance those LORs 114 travel through a patient 104 than the distance the other LORs 112 travel through the patient 104.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for increasing the sensitivity of a positron emission tomography (PET) scanner to coincidence events within a subset of azimuth angles of said PET scanner, said apparatus comprising:

a first set of detectors around a space for receiving a patient, said space having a longitudinal axis, said first set of detectors responsive to coincidence events within said patient generating lines of response within a first set of azimuth angles and within a second set of azimuth angles, said first set of detectors being in communication with a processing system of the PET scanner that generates lines of response in response to detected coincidence events; and a second set of detectors positioned around said space such that said second set of detectors are responsive to coincidence events generating lines of response within said first set of azimuth angles and are not responsive to coincidence events generating lines of response within said second set of azimuth angles, said second set of detectors being in communication with said processing system of the PET scanner;

whereby said second set of detectors compensates for greater attenuation of coincidence events traveling along lines of response within said first set of azimuth angles relative to coincidence events traveling along lines of response within said second set of azimuth angles.

2. The apparatus of claim 1 wherein said processing system combines said plurality of lines of response within said first set of azimuth angles and within said second set of azimuth angles to reconstruct an image.

3. The apparatus of claim 1 wherein said first set of detectors includes at least one ring with a plurality of detectors distributed around the circumference of said at least one ring.

4. The apparatus of claim 1 wherein said second set of detectors includes at least one partial ring with a plurality of detectors distributed around the circumference of said at least one partial ring, said at least one partial ring including a first arc and a second arc, said first arc positioned substantially diametrically opposite said second arc.

5. The apparatus of claim 1 wherein said second set of detectors are distributed substantially evenly on diametrically opposite sides of said space.

6. The apparatus of claim 1 wherein said second set of detectors includes a first partial ring positioned adjacent to said first set of detectors, and said second set of detectors further includes a second partial ring positioned adjacent to said first set of detectors and proximal to said first partial ring.

7. An apparatus for increasing the sensitivity of a positron emission tomography (PET) scanner to coincidence events within a subset of azimuth angles of said PET scanner, said apparatus comprising:
 a first set of detectors responsive to coincidence events within said patient generating a plurality of lines of response within a first set of azimuth angles, said first set of detectors being in communication with a processing system of the PET scanner, said first set of detectors having a first detector length;
 a second set of detectors responsive to coincidence events within said patient generating a plurality of lines of response within a second set of azimuth angles, said second set of detectors being in communication with said processing system of the PET scanner, said second set of detectors having a second detector length, said first detector length being greater than said second detector length; and
 said first and second set of detectors located around a space for receiving a patient, said space having a longitudinal axis, each of said first detector length and said second detector length being measured along a line substantially parallel to said longitudinal axis;
 whereby said second set of detectors compensates for greater attenuation of coincidence events traveling along lines of response within said first set of azimuth angles relative to coincidence events traveling along lines of response within said second set of azimuth angles.

8. The apparatus of claim 7 wherein said processing system combines said plurality of lines of response within said first set of azimuth angles and within said second set of azimuth angles to reconstruct an image.

9. The apparatus of claim 7 wherein said first set of detectors includes at least one first panel detector and said second set of detectors includes at least one second panel detector.

10. An apparatus for increasing the sensitivity of a positron emission tomography (PET) scanner to coincidence events within a subset of azimuth angles of said PET scanner, said apparatus comprising:
 a set of detectors adapted to rotate about a space for receiving a patient, said set of detectors being in communication with a processing system of the PET scanner, said set of detectors including at least one first detector and at least one second detector, said at least one first detector being positioned substantially diametrically opposite said at least one second detector, said set of detectors having a first dwell time when said set of detectors is positioned to be responsive to coincidence events within said patient generating a plurality of lines of response within a first set of azimuth angles, said set of detectors having a second dwell time when said set of detectors is positioned to be responsive to coincidence events within said patient generating a plurality of lines of response within a second set of azimuth angles, said first dwell time being greater than said second dwell time;
 whereby said second set of detectors compensates for greater attenuation of coincidence events traveling along lines of response within said first set of azimuth angles relative to coincidence events traveling along lines of response within said second set of azimuth angles.

11. The apparatus of claim 10 wherein said processing system combines said plurality of lines of response within said first set of azimuth angles and within said second set of azimuth angles to reconstruct an image.

12. The apparatus of claim 10 wherein said set of detectors detects coincidence events generating lines of response within said first set of azimuth angles for a longer time than said set of detectors detects coincidence events generating lines of response within said second set of azimuth angles.

13. The apparatus of claim 10 wherein said set of detectors includes a plurality of detectors selected from a group of a set of partial rings and a set of panel detectors.

14. An apparatus for increasing the sensitivity of a positron emission tomography (PET) scanner to coincidence events within a subset of azimuth angles of said PET scanner, said apparatus comprising:
 a set of detectors responsive to coincidence events generating lines of response within a first set of azimuth angles and within a second set of azimuth angles, said set of detectors being in communication with a processing system of the PET scanner; wherein
 said set of detectors being configured to detect a greater number coincidence events associated with lines of response within said first set of azimuth angles than coincidence events associated with lines of response within said second set of azimuth angles.

15. The apparatus of claim 14 wherein said set of detectors includes at least one detector ring and at least one partial detector ring.

16. The apparatus of claim 14 wherein said set of detectors includes at least one pair of first detector panels having an axial length longer than at least one pair of second detector panels of said set of detectors.

17. The apparatus of claim 14 wherein said set of detectors includes a pair of rotating detector assemblies, said pair of rotating detector assemblies adapted to be positioned to be responsive to coincidence events associated with lines of response within said first set of azimuth angles for a greater amount of time than when said pair of rotating detector assemblies is positioned to be responsive to coincidence events associated with lines of response within said second set of azimuth angles.

18. The apparatus of claim 17 wherein said set of detectors is selected from the group consisting of a plurality of panels and a plurality of partial rings.

19. A method of performing positron emission tomography, comprising detecting a greater number of coincidence events undergoing a greater amount of attenuation than coincidence events undergoing a lesser amount of attenuation.

* * * * *